United States Patent [19]

Hairston

[11] Patent Number: 5,518,213
[45] Date of Patent: May 21, 1996

[54] ARM CASTING STAND

[75] Inventor: William S. Hairston, P.O. Box 1761, Salisburg, N.C. 28145

[73] Assignee: William S. Hairston, Greensboro, N.C.

[21] Appl. No.: 51,993

[22] Filed: Jun. 4, 1993

[51] Int. Cl.$^6$ .............................. F16M 13/00; B68G 5/00
[52] U.S. Cl. .................................. 248/118.3; 248/121
[58] Field of Search ................. 248/118, 118.1, 248/118.3, 118.5, 125, 121, 146, 918; 128/881, 878, 877, 892

[56] References Cited

U.S. PATENT DOCUMENTS

| | | | |
|---|---|---|---|
| 443,839 | 12/1890 | Steinhauer | 248/118 |
| 1,025,476 | 5/1912 | Mellen | 248/118 |
| 2,614,558 | 10/1952 | Lovell | 248/118 |
| 2,630,288 | 3/1953 | Eubanks, Sr. | 248/118 |
| 3,380,694 | 4/1968 | Branner | 248/118 |
| 4,069,995 | 1/1978 | Miller | 248/118.1 |
| 4,163,536 | 8/1979 | Heller et al. | 248/118 |
| 4,564,164 | 1/1986 | Allen et al. | 248/118 |
| 4,909,264 | 3/1990 | Wadsworth, III et al. | 128/878 X |
| 4,997,054 | 3/1991 | Denny et al. | 248/118 X |

FOREIGN PATENT DOCUMENTS 1230670  5/1971  United Kingdom .................... 248/121

*Primary Examiner*—Karen J. Chotkowski

[57] ABSTRACT

The Arm Casting Stand is a device that is to be used by anyone trained in applying a short arm cast. Comprised of an elbow cuff to support the arm while the cast is being applied. There is a single pole that is permanently attached to the cuff. This pole has six holes for adjustment up or down for comfort. This pole fits into the center pole that is attached to a triangle base. Attached to the base are three inverted "L" shaped poles that are attached to the center pole. The center pole has a hole in it for the pin that holds the adjustment pole in place. The cuff that holds the elbow has different sizes for the comfort of the patient. This device is light weight and portable.

1 Claim, 2 Drawing Sheets

ARM CASTING STAND

BACKGROUND OF THE INVENTION

The arm casting stand of the present invention is a support device for the casting of the arm from about 2 inches below the elbow to the knuckles of the hand. Heretofore, there has not been an arm casting stand that is lightweight and of a simple and practical construction which is efficient and dependable in use. Generally, a wooden block or a U-shaped pillow are used to support a patient's arm while a cast is being applied. The stand of the present invention is comfortable to the patient and saves work and time for the orthopedic technician or doctor while applying a short arm cast. It is neat and attractive in appearance, relatively inexpensive to manufacture, maintenance free and will adapt well for the purpose it was intended.

SUMMARY OF THE INVENTION

The present invention relates to a support stand for use in short arm casting and specifically for improving the comfort of the patient. Using the arm casting stand, only one technician or doctor is required to apply a short arm cast, instead of two as in some cases now.

DESCRIPTION OF THE PREFERRED EMBODIMENTS

Figure 1:
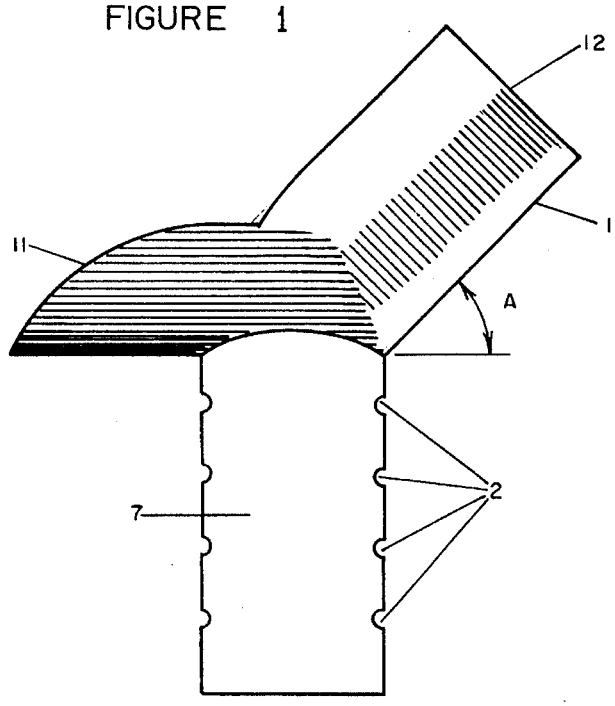
FIG. 1 is a side view of the arm casting stand of the present invention.
Figure 1:
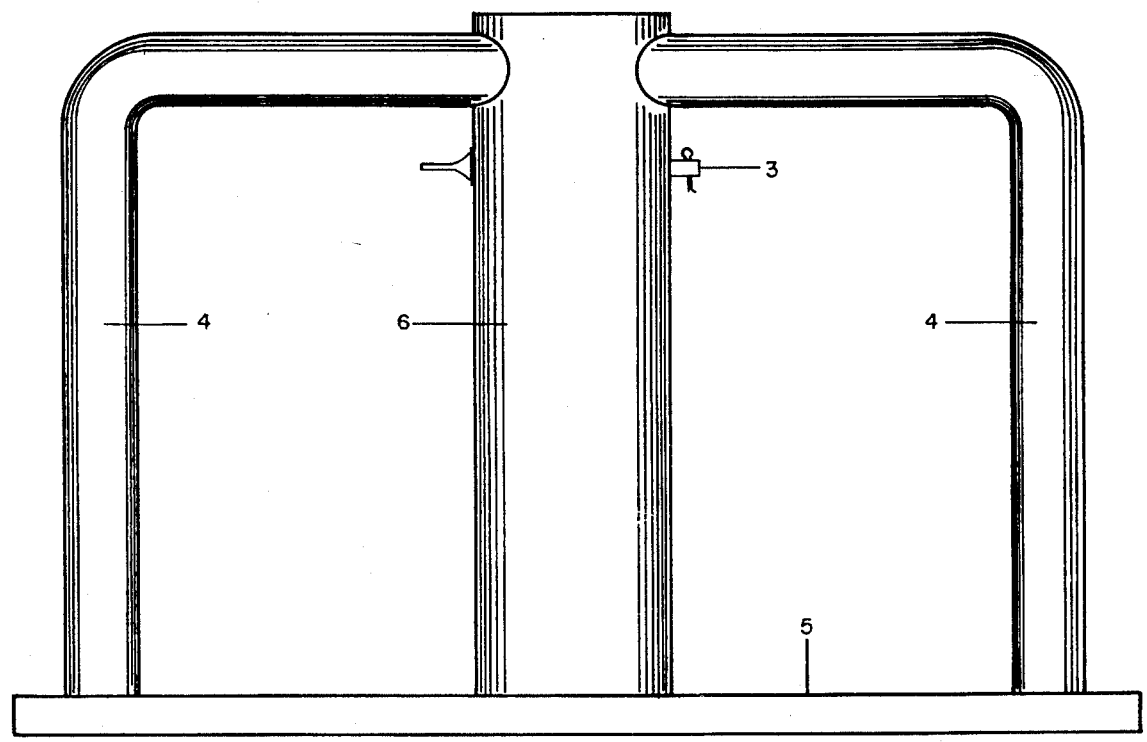

The arm casting stand as shown in FIG. 1 has a planar triangular shaped base 5. Extending upwardly from the base 5 is a center pole formed of a first telescoping section 6 and a second telescoping section 7. An elbow support cuff 1 for supporting a patient's elbow is disposed on the upper end of the center pole.

Figure 2:
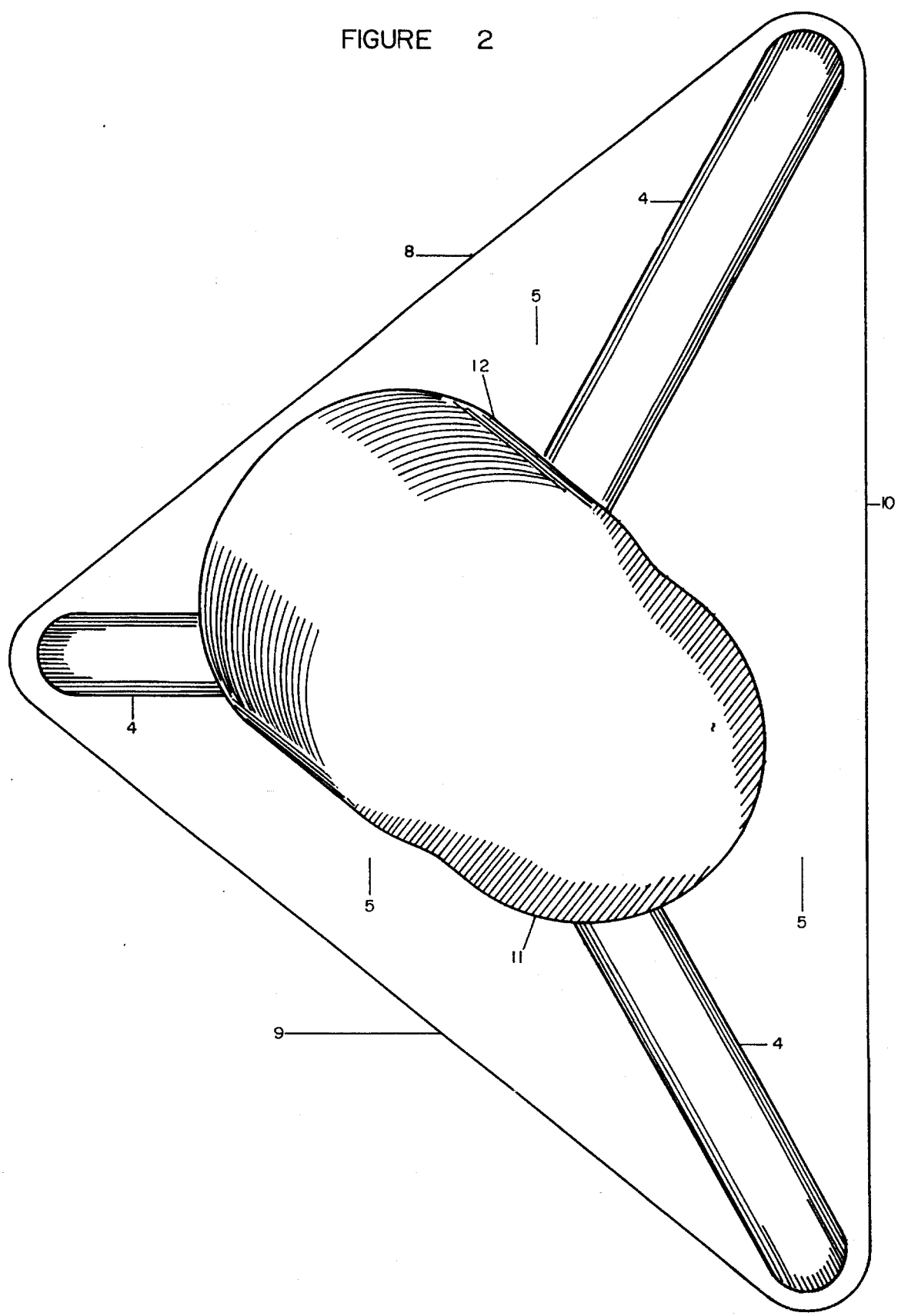
FIG. 2 is a top view of the arm casting stand.

The planar triangular shaped base has three sides 8, 9, 10. In a preferred embodiment shown in FIG. 2, the sides of the base have corresponding dimensions of 10½ inches, 9½ inches and 9½ inches.

The first telescoping section 6 forms a socket which is attached to the base. Three radiating L-shaped support braces 4 extend upwardly from the triangular shaped base and inwardly to a top edge of the socket 6. In a preferred embodiment the support braces have a cross sectional diameter of ¾ inches while the socket has a cross sectional diameter of 1½ inches and a height of 6⅜ inches.

The second telescoping section 7 has a plurality of aligned apertures 2. A pin 3 extends through a pair of aligned apertures 2 in the second section 7 and through the socket 6 to selectively lock the sections together. The height of the elbow support cuff 1 can be adjusted for the patient's comfort as a cast is applied to the arm. The patient may be on a stretcher or in a sitting position during casting.

The elbow support cuff 1 is disposed at the top of the second telescoping section. The cuff 1 is shaped to receive the support the elbow of a patient having a broken arm. The cuff 1 is a trough-shaped member having an inner surface that extends parallel to the triangular support base and then bends upwardly at an angle A of 45 degrees. The trough-shaped member has side walls defined by a generally horizontal portion 11 having a semicircular shape and an upwardly angled portion 12. In a preferred embodiment the second telescoping section has a length of 6 inches and the cuff has a height of 5½ inches. The radius of curvature of the inner surface of the trough-shaped member is 3½ inches.

The arm casting stand, including the base, telescoping sections, support braces and cuff is made from polyvinyl chloride (PVC). It is lightweight and portable for use.

What is claimed is:

1. An arm casting stand for use by an orthopedic technician when casting the arm of a patient, wherein the arm casting stand comprises:

a generally planar triangle base disposed in a horizontal plane;

a center pole having a first and second telescoping section, wherein the first telescopic section is a socket disposed on the triangle base which is adapted for receiving the second telescoping section therein; the socket is reinforced in a vertical position on the triangle base by three radiating support braces extending outwardly from an upper end of the socket and downwardly to respective apexes of the triangle base;

a height adjustment means provides vertical adjustment of the second telescopic section relative to the first telescopic section;

an elbow support cuff is disposed on an upper end of the second telescoping section and is shaped to receive and support the elbow of a patient therein, the elbow support cuff comprises a trough shaped member having a longitudinal axis which extends generally parallel to the horizontal plane of the triangle base, the trough shaped member further comprising an elbow support surface wherein the elbow support surface of the trough extends parallel to the longitudinal axis a distance then extends upwards at a 45 degree angle from the longitudinal axis of the trough shaped member forming a 45 degree bend in the elbow support surface of the trough shaped member for receiving a patient's elbow therein.

* * * * *